United States Patent
Pascal et al.

(10) Patent No.: US 11,986,241 B2
(45) Date of Patent: May 21, 2024

(54) AUTOMATIC OPTICAL PATH ADJUSTMENT IN HOME OCT

(71) Applicant: Notal Vision Ltd., Tel Aviv (IL)

(72) Inventors: Amit Pascal, Haifa (IL); Omer Rafaeli, Udim (IL); Yair Alster, Tel-Aviv (IL); Gidon Goren-Gratzyani, Givatayim (IL)

(73) Assignee: Notal Vision, Ltd., Tel Aviv (IL)

( * ) Notice: Subject to any disclaimer, the term of this patent is extended or adjusted under 35 U.S.C. 154(b) by 83 days.

(21) Appl. No.: 17/900,304

(22) Filed: Aug. 31, 2022

(65) Prior Publication Data

US 2023/0101855 A1  Mar. 30, 2023

Related U.S. Application Data

(63) Continuation of application No. 16/802,200, filed on Feb. 26, 2020, now Pat. No. 11,464,408, which is a
(Continued)

(51) Int. Cl.
*A61B 3/14*  (2006.01)
*A61B 3/10*  (2006.01)
(Continued)

(52) U.S. Cl.
CPC ............ *A61B 3/102* (2013.01); *A61B 3/14* (2013.01); *A61B 5/004* (2013.01); *A61B 5/0066* (2013.01);
(Continued)

(58) Field of Classification Search
CPC ......... A61B 3/102; A61B 3/14; A61B 3/0025; A61B 5/004; A61B 5/0066; A61B 5/0064;
(Continued)

(56) References Cited

U.S. PATENT DOCUMENTS 5,094,521 A   3/1992  Jolson et al.
5,838,424 A   11/1998 Wawro et al.
(Continued)

FOREIGN PATENT DOCUMENTS

JP   2012213602 A   11/2012
JP   2013212173 A   10/2013
(Continued)

OTHER PUBLICATIONS

Cense et al., "In Vivo Birefringence and Thickness Measurements of the Human Retinal Nerve Fiber Layer Using Polarization-Sensitive Optical Coherence Tomography", Journal Of Biomedical Optics, vol. 9, No. 1, Jan. 1, 2004, pp. 121-125.
(Continued)

*Primary Examiner* — William R Alexander
(74) *Attorney, Agent, or Firm* — Kilpatrick Townsend & Stockton LLP

(57) ABSTRACT

Retinal imaging systems and related methods employ a user specific approach for controlling the reference arm length in an optical coherence tomography (OCT) imaging device. A method includes generating a signal indicative of a position of a feature of a user's head relative to an OCT imaging device. A user specific reference arm adjustment length range for the user within a reference arm adjustment length range of the OCT device is determined based on the signal. A reference arm length adjustment module is controlled during an imaging of the retina to vary a reference arm length of the OCT imaging device within the user specific reference arm adjustment length range to identify an imaging reference arm length for which an OCT image detector of the OCT imaging device produces an OCT signal corresponding to the retina of the user.

20 Claims, 9 Drawing Sheets

Related U.S. Application Data continuation of application No. 16/424,246, filed on May 28, 2019, now Pat. No. 10,595,722.

(60) Provisional application No. 62/740,781, filed on Oct. 3, 2018.

(51) Int. Cl.
    *A61B 5/00*     (2006.01)
    *G01B 9/02*     (2022.01)
    *G01B 9/02015*     (2022.01)

(52) U.S. Cl.
    CPC ....... *G01B 9/0203* (2013.01); *G01B 9/02043* (2013.01)

(58) Field of Classification Search
    CPC .............. G01B 9/0203; G01B 9/02043; G01B 9/02031; G01B 9/02091; G01B 9/02063; G01B 9/02064; G01B 9/02076; G01B 2290/35
    USPC ........................................................ 351/206
    See application file for complete search history.

(56) References Cited

U.S. PATENT DOCUMENTS

| | | | |
|---|---|---|---|
| 6,149,275 A | 11/2000 | O'Shea | |
| 6,980,363 B1 | 12/2005 | Takagi et al. | |
| 7,270,413 B2 | 9/2007 | Hirohara et al. | |
| 7,942,527 B2 | 5/2011 | Olivier et al. | |
| 8,054,468 B2 | 11/2011 | De Boer et al. | |
| 8,064,989 B2 | 11/2011 | Brown et al. | |
| 8,098,278 B2 | 1/2012 | Yumikake et al. | |
| 8,123,354 B2 | 2/2012 | Olivier et al. | |
| 8,348,429 B2 | 1/2013 | Walsh et al. | |
| 8,374,684 B2 | 2/2013 | Buckland et al. | |
| 8,384,908 B2 | 2/2013 | Sugita et al. | |
| 8,398,236 B2 | 3/2013 | Juhasz et al. | |
| 8,421,855 B2 | 4/2013 | Buckland et al. | |
| 8,459,794 B2 | 6/2013 | Juhasz et al. | |
| 8,500,725 B2 | 8/2013 | Raksi | |
| 8,534,835 B2 | 9/2013 | Murata et al. | |
| 8,534,837 B2 | 9/2013 | Sayeram et al. | |
| 8,668,336 B2 | 3/2014 | Buckland et al. | |
| 8,804,127 B2 | 8/2014 | Shimoyama et al. | |
| 8,820,931 B2 | 9/2014 | Walsh et al. | |
| 8,842,287 B2 | 9/2014 | Yazdanfar et al. | |
| 8,860,796 B2 | 10/2014 | Buckland et al. | |
| 8,960,903 B2 | 2/2015 | Horn et al. | |
| 8,960,905 B2 | 2/2015 | Aoki et al. | |
| 9,044,166 B2 | 6/2015 | Murata et al. | |
| 9,144,379 B1 | 9/2015 | Sims | |
| 9,149,182 B2 | 10/2015 | Walsh et al. | |
| 9,170,087 B2 | 10/2015 | Makihira et al. | |
| 9,173,563 B2 | 11/2015 | Buckland et al. | |
| 9,186,057 B2 | 11/2015 | Borycki et al. | |
| 9,192,295 B1 | 11/2015 | Hathaway et al. | |
| 9,273,950 B2 | 3/2016 | Yazdanfar et al. | |
| 9,277,859 B2 | 3/2016 | Oyaizu et al. | |
| 9,277,860 B2 | 3/2016 | Komine et al. | |
| 9,314,154 B2 | 4/2016 | Palanker et al. | |
| 9,420,947 B2 | 8/2016 | Wei et al. | |
| 9,427,151 B2 | 8/2016 | Horn et al. | |
| 9,492,079 B2 | 11/2016 | Walsh et al. | |
| 9,538,916 B2 | 1/2017 | Muto | |
| 9,565,999 B2 | 2/2017 | Takai | |
| 9,572,484 B2 | 2/2017 | Palanker et al. | |
| 9,622,658 B2 | 4/2017 | Hart et al. | |
| 9,814,383 B2 | 11/2017 | Hart et al. | |
| 9,888,841 B2 | 2/2018 | Hogan | |
| 9,907,466 B2* | 3/2018 | Kowal ................. A61B 3/0083 |
| 10,048,055 B2 | 8/2018 | Lim et al. | |
| 10,092,180 B2 | 10/2018 | Hart et al. | |
| 10,165,941 B2 | 1/2019 | Walsh et al. | |
| 10,251,549 B2 | 4/2019 | Sarunic et al. | |
| 10,258,229 B2* | 4/2019 | Kowal ................... A61B 3/152 |
| 10,314,480 B2 | 6/2019 | Ishiai | |
| 10,327,632 B2 | 6/2019 | Horn | |
| 10,568,503 B2 | 2/2020 | Bublitz et al. | |
| 10,610,096 B2 | 4/2020 | Scheibler et al. | |
| 10,653,309 B2 | 5/2020 | Shimozato et al. | |
| 10,653,311 B1 | 5/2020 | Pascal et al. | |
| 10,653,314 B2 | 5/2020 | Pascal et al. | |
| 11,118,894 B2 | 9/2021 | Tearney et al. | |
| 11,129,525 B2* | 9/2021 | Westphal ............... A61B 3/102 |
| 2003/0063386 A1 | 4/2003 | Slawson et al. | |
| 2008/0094613 A1 | 4/2008 | De Boer et al. | |
| 2008/0259274 A1 | 10/2008 | Chinnock | |
| 2009/0180074 A1 | 7/2009 | Benyamini et al. | |
| 2009/0268020 A1 | 10/2009 | Buckland et al. | |
| 2009/0268161 A1 | 10/2009 | Hart et al. | |
| 2010/0014051 A1 | 1/2010 | Rathjen | |
| 2011/0299034 A1* | 12/2011 | Walsh ..................... A61B 3/132 351/206 |
| 2013/0033593 A1 | 2/2013 | Chinnock et al. | |
| 2013/0162948 A1 | 6/2013 | Yazdanfar et al. | |
| 2013/0162978 A1 | 6/2013 | Yazdanfar et al. | |
| 2013/0235344 A1 | 9/2013 | Buckland et al. | |
| 2014/0002792 A1 | 1/2014 | Filar | |
| 2014/0009741 A1 | 1/2014 | Levien et al. | |
| 2014/0028974 A1 | 1/2014 | Tumlinson | |
| 2014/0125952 A1 | 5/2014 | Buckland et al. | |
| 2014/0132924 A1 | 5/2014 | Sagano et al. | |
| 2014/0240674 A1 | 8/2014 | Wei et al. | |
| 2014/0285811 A1 | 9/2014 | Brennan et al. | |
| 2014/0340642 A1 | 11/2014 | You et al. | |
| 2015/0292860 A1 | 10/2015 | Podoleanu et al. | |
| 2015/0294147 A1 | 10/2015 | Wisweh | |
| 2015/0305618 A1 | 10/2015 | Buckland et al. | |
| 2015/0313467 A1 | 11/2015 | Sakai et al. | |
| 2016/0026847 A1 | 1/2016 | Vugdelija et al. | |
| 2016/0135681 A1 | 5/2016 | Wakil et al. | |
| 2016/0143529 A1 | 5/2016 | Miyashita et al. | |
| 2016/0183788 A1 | 6/2016 | Abramoff et al. | |
| 2017/0042422 A1 | 2/2017 | Sakai et al. | |
| 2017/0049318 A1 | 2/2017 | Walsh et al. | |
| 2017/0071466 A1* | 3/2017 | Kowal ................. A61B 3/0075 |
| 2017/0143202 A1 | 5/2017 | Palanker et al. | |
| 2017/0172407 A1* | 6/2017 | Kowal ................... A61B 3/1225 |
| 2017/0215725 A1 | 8/2017 | Ishiai | |
| 2017/0224208 A1 | 8/2017 | Bublitz et al. | |
| 2017/0227350 A1 | 8/2017 | Sarunic et al. | |
| 2017/0251920 A1 | 9/2017 | Tokuda et al. | |
| 2018/0020912 A1 | 1/2018 | Bublitz et al. | |
| 2018/0296087 A1 | 10/2018 | Carrasco-Zevallos et al. | |
| 2019/0090733 A1 | 3/2019 | Walsh et al. | |
| 2019/0090735 A1 | 3/2019 | Fujii et al. | |
| 2019/0254514 A1* | 8/2019 | Westphal ............... A61B 3/102 |
| 2019/0254518 A1 | 8/2019 | Rafaeli et al. | |
| 2019/0313895 A1 | 10/2019 | Hayashi et al. | |
| 2019/0368861 A1 | 12/2019 | Wax et al. | |
| 2019/0380573 A1 | 12/2019 | Bublitz | |
| 2021/0025690 A1 | 1/2021 | Tearney et al. | |
| 2021/0038071 A1 | 2/2021 | Tatara et al. | |

FOREIGN PATENT DOCUMENTS

| | | |
|---|---|---|
| JP | 2015096240 A | 5/2015 |
| JP | 2016536075 A | 11/2016 |
| JP | 2016220735 A | 12/2016 |
| JP | 2018509983 A | 4/2018 |
| JP | 2018126257 A | 8/2018 |
| WO | 2016004385 A1 | 1/2016 |
| WO | 2019147871 A1 | 8/2019 |
| WO | 2019246412 A1 | 12/2019 |
| WO | 2020056454 A1 | 3/2020 |

OTHER PUBLICATIONS

Chakravarthy et al., "Automated Identification of Lesion Activity in Neovascular Age-Related Macular Degeneration", Ophthalmology, vol. 123, No. 8, Aug. 2016, 6 pages.

(56) References Cited

OTHER PUBLICATIONS

Iftimia et al., "Adaptive Ranging for Optical Coherence Tomography", Optics Express, vol. 12, No. 17, Jan. 1, 2004, pp. 4025-4034.
Maguluri et al., "Three Dimensional Tracking for Volumetric Spectral-Domain Optical Coherence Tomography", Optics Express, vol. 15, No. 25, Jan. 1, 2007, pp. 16808-16817.

\* cited by examiner

FOV cut
Pupil at the nominal position
3mm pupil actual FOV 20 deg on retina

FOV cut
Pupil 15mm off the nominal position
3mm pupil actual FOV 10 deg on retina

AUTOMATIC OPTICAL PATH ADJUSTMENT IN HOME OCT

CROSS-REFERENCES TO RELATED APPLICATIONS

The present application is a Continuation of U.S. patent application Ser. No. 16/802,200 filed Feb. 26, 2020 (now U.S. Pat. No. 11,464,408); which is a Continuation of U.S. patent application Ser. No. 16/424,246 filed May 28, 2019 (now U.S. Pat. No. 10,595,722); which claims the benefit of U.S. Provisional Appln No. 62/740,781 filed Oct. 3, 2018, the full disclosures which are incorporated herein by reference in their entirety for all purposes.

BACKGROUND

Macular degeneration is the leading cause of vision loss in the United States of America. In macular degeneration, the central portion of the retina (a.k.a., the macula) deteriorates. When healthy, the macula collects and sends highly detailed images to the brain via the optic nerve. In early stages, macular degeneration typically does not significantly affect vision. If macular degeneration progresses beyond the early stages, vision becomes wavy and/or blurred. If macular degeneration continues to progress to advanced stages, central vision may be lost.

Although macular degeneration is currently considered to be incurable, treatments do exist that may slow the progression of the disease so as to prevent severe loss of vision. Treatment options include injection of an anti-angiogenic drug into the eye, laser therapy to destroy an actively growing abnormal blood vessel(s), and photodynamic laser therapy, which employs a light-sensitive drug to damage an abnormal blood vessel(s). Early detection of macular degeneration is of paramount importance in preventing advanced progression of macular degeneration prior to treatment to inhibit progression of the disease.

Early detection of macular degeneration can be accomplished using a suitable retinal imaging system. For example, Optical Coherence Tomography (OCT) is a non-invasive imaging technique relying on low coherence interferometry that can be used to generate a cross-sectional image of the macula. The cross-sectional image of the macula shows if the layers of the macula are distorted and can be used to monitor whether distortion of the layers of the macula has increased or decreased relative to an earlier cross-sectional image to assess the impact of treatment of the macular degeneration.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Ophthalmic imaging systems and related methods employ a viewer assembly to restrain a user's head in a substantially fixed position and orientation relative to an optical coherence tomography (OCT) imaging device and a user specific approach for controlling the reference arm length in the (OCT) imaging device to image the user's retina. In many embodiments, the OCT imaging device includes a reference arm length adjustment module that is controlled to vary the reference arm length. In many embodiments, the user engages the user's head with the viewer assembly, thereby restraining the position of the user's retina relative to the OCT imaging device. Due to variation between users in the position of a user's retina relative to the user's facial features (e.g., forehead, cheek) engaged with the viewer assembly, as well as possible variation in the relative position between a user's head and the viewer assembly, the sample arm length to any particular user's retina can be within a relatively large range. In many embodiments, a user specific range of reference arm lengths is used during imagining of a user's retina. The user specific range of reference arm lengths is substantially smaller than a reference arm adjustment range of the reference arm length adjustment module. The use of the smaller user specific range of reference arm lengths during imaging of the user's retina substantially reduces the amount of time expended scanning of the reference arm length to find the reference arm length at which the OCT image detector generates the OCT signal for the user's retina, thereby substantially reducing the total amount of time required to image the user's retina. Also, by employing a user specific range of reference arm lengths, the OCT imaging system can be simplified relative to more complex OCT imaging systems that include a positioning system to adjust the distance between the OCT imaging device and the user's retina.

Thus, in one aspect, an ophthalmic imaging system for imaging a retina includes an optical coherence tomography (OCT) imaging device, a housing to which the OCT imaging device is attached, a viewer assembly coupled with the housing, and a control unit. The OCT imaging device includes a sample arm optical path, an OCT image detector, a reference arm optical path, and a reference arm length adjustment module. The reference arm optical path has a reference arm length. The reference arm length adjustment module is controllable to vary the reference arm length over a reference arm length adjustment range. The viewer assembly is configured to engage a user's head to restrain the user's head relative to the housing so that the sample arm optical path extends to the user's retina. The control unit is operatively connected to the OCT image detector and the reference arm length adjustment module. The control unit is configured to store a user specific range of reference arm lengths that covers a smaller range of reference arm lengths than the reference arm length adjustment range. The control unit is configured to control the reference arm length adjustment module to vary the reference arm length to search within the user specific range of reference arm lengths to identify a reference arm length for which the OCT image detector produces an OCT signal corresponding to the user's retina.

Any suitable approach, such as those described herein, can be used to determine a suitable user specific range of reference path arm lengths for a particular user for use in the ophthalmic imaging system. For example, as described herein, the larger reference arm path length adjustment range of the adjustable reference arm module can be searched during an initial imaging of the user's retina to identify a reference path length for which the OCT image detector 38 produces an OCT signal corresponding to the user's retina. The identified reference path length for the initial imaging of the user's retina can then be used to formulate a suitable user specific range of reference path arm lengths for use in subsequent imaging sessions of the specific user's retina. Alternatively, a suitable user specific range of reference path arm lengths for any particular user can be predetermined. For example, the user specific range of reference path arm lengths can be based on spatial information about one or more facial features of the user. In some embodiments, the one or more facial features of the user upon which the user specific range of reference path arm lengths can be based include one or more of a forehead of the user, one or more cheeks of the user, a cornea of an eye of the user including the retina of the user, and a lateral orbital rim of the user. The spatial information about one or more facial features of the user is generated via one or more of: (a) three-dimensional scanning of the one or more facial features of the user, (b) caliper measurement of the one or more facial features of the user relative to an eye of the user that includes the retina of the user, (c) a cast mask of the one or more facial features of the user, (d) an axial length of the eye of the user that includes the retina of the user, (e) ultrasound measurement of the axial length of the eye of the user that includes the retina of the user, and (f) OCT measurement of the axial length of the eye of the user that includes the retina of the user.

In many embodiments, the ophthalmic imaging system lacks a mechanism to adjust the length of the sample arm optical path. For example, in many embodiments, the ophthalmic imaging system includes an objective lens assembly and does not include an adjustment mechanism configured to adjust a distance between the user's retina and the objective lens assembly.

The lack of an adjust mechanism configured to adjust a distance between the user's retina and the objective lens assembly results in a reduced field of view on some user's retinas. To account for such a reduced field of view, in some embodiments, the ophthalmic imaging system is configured to image a field of view on the user's retina equal to or less than 15 degrees for the reference arm length equal to any length within the reference arm length adjustment range. In some embodiments, the ophthalmic imaging system is configured to image a field of view on the user's retina equal to or less than 10 degrees for the reference arm length equal to any length within the reference arm length adjustment range.

The OCT imaging device can have a relatively small image depth. For example, in some embodiments, the OCT imaging device has an image depth of no more than 3 mm.

The OCT imaging device can have a relatively large sensitivity roll-off. For example, in some embodiments, the OCT imaging device has a sensitivity roll off of not better than −3 db at 2 mm.

The user specific range of reference arm lengths can be substantially smaller than the reference arm length adjustment range of the reference arm length adjustment module. For example, in many embodiments, the user specific range of reference arm lengths is less than half of the reference arm length adjustment range. In some embodiments, the user specific range of reference arm lengths is less than one-quarter of the reference arm length adjustment range.

The control unit can have any suitable configuration. For example, in many embodiments, the control unit is configured to receive input of the user specific range of reference arm lengths and store the user specific range of reference arm lengths in a memory device. In some embodiments, the control unit is configured to determine the user specific range of reference arm lengths by controlling the reference arm length adjustment module during an imaging of the user's retina to vary the reference arm length to search within the reference arm length adjustment range to identify a user specific imaging reference arm length for which the OCT image detector produces an OCT signal corresponding to the user's retina. In some embodiments, the control unit determines the user specific range of reference arm lengths based on the user specific imaging reference arm length.

The reference arm length adjustment range can encompass a relatively large range of reference arm lengths. For example, in many embodiments, the reference arm length adjustment range encompasses at least a 20 mm range of reference arm lengths. The reference arm length adjustment range can encompass at least a 30 mm range of reference arm lengths. In some embodiments, the reference arm length adjustment range encompasses at least a 40 mm range of reference arm lengths.

The user specific range of reference arm lengths can encompass a relatively small range of reference arm lengths. For example, in many embodiments, the user specific range of reference arm lengths encompasses less than a 10 mm range of reference arm lengths. The user specific range of reference arm lengths can encompass less than a 6 mm range of reference arm lengths. In some embodiments, the user specific range of reference arm lengths encompasses less than a 4 mm range of reference arm lengths.

In some embodiments, the ophthalmic imaging system includes a sensor that generates a signal indicative of a position of a feature of the user's head relative to the housing. In such embodiments, the control unit can be configured to determine the user specific range of reference arm lengths based on the signal indicative of the position of the feature of the user's head relative to the housing.

In some embodiments, the ophthalmic imaging system includes a sensor that generates a signal indicative of a position of a feature of the user's forehead relative to the housing. In such embodiments, the control unit can be configured to determine the user specific range of reference arm lengths based on the signal indicative of the position of the feature of the user's forehead relative to the housing.

In some embodiments, the ophthalmic imaging system includes a sensor that generates a signal indicative of a position of a feature of an eye of the user relative to the housing, wherein the eye includes the user's retina. In such embodiments, the control unit can be configured to determine the user specific range of reference arm lengths based on the signal indicative of a position of a feature of the eye of the user relative to the housing.

In many embodiments, the viewer assembly includes a compliant member that accommodates an amount of relative movement between the user head and the OCT device. For example, in many embodiments, the viewer assembly includes a compliant member having a thickness that can change up to 10 mm in response to change in pressure applied to the viewer assembly by the user's head. In some embodiments, the viewer assembly includes a compliant member having a thickness that can change up to 20 mm in response to change in pressure applied to the viewer assembly by the user's head.

In many embodiments, the ophthalmic imaging system includes a focusing module that is controlled by the control unit to focus sample light transmitted over the sample arm optical path onto the user's retina. A focus setting of the focusing module corresponding to the user specific imaging reference arm length can be employed during imaging of the user's retina.

In another aspect, a method of imaging a retina is provided. The method includes restraining, via a viewer assembly coupled with a housing and engaged with a user's head, the user's head relative to the housing so that a sample arm optical path of an optical coherence tomography (OCT) imaging device attached to the housing extends to the user's retina. The method includes controlling, by a control unit, a reference arm length adjustment module of the OCT imaging device to vary a reference arm length of a reference arm optical path of the OCT imaging device to search a user specific range of reference arm lengths to identify a reference arm length for which the OCT image detector produces an OCT signal corresponding to the user's retina. The reference arm length adjustment module is controllable to vary the reference arm length over a reference arm length adjustment range. The user specific range of reference arm lengths covers a smaller range of reference arm lengths than the reference arm length adjustment range. The method includes imaging, by the OCT imaging device, the user's retina.

Any suitable approach, such as those described herein, can be used to determine a suitable user specific range of reference path arm lengths for a particular user for use in the method of imaging the retina. For example, as described herein, the larger reference arm path length adjustment range of the adjustable reference arm module can be searched during an initial imaging of the user's retina to identify a reference path length for which the OCT image detector 38 produces an OCT signal corresponding to the user's retina. The identified reference path length for the initial imaging of the user's retina can then be used to formulate a suitable user specific range of reference path arm lengths for use in subsequent imaging sessions of the specific user's retina. Alternatively, a suitable user specific range of reference path arm lengths for any particular user can be predetermined. For example, the user specific range of reference path arm lengths can be based on spatial information about one or more facial features of the user. In some embodiments, the one or more facial features of the user upon which the user specific range of reference path arm lengths can be based include one or more of a forehead of the user, one or more cheeks of the user, a cornea of an eye of the user including the retina of the user, and a lateral orbital rim of the user. The spatial information about one or more facial features of the user is generated via one or more of: (a) three-dimensional scanning of the one or more facial features of the user, (b) caliper measurement of the one or more facial features of the user relative to an eye of the user that includes the retina of the user, (c) a cast mask of the one or more facial features of the user, (d) an axial length of the eye of the user that includes the retina of the user, (e) ultrasound measurement of the axial length of the eye of the user that includes the retina of the user, and (f) OCT measurement of the axial length of the eye of the user that includes the retina of the user.

In many embodiments, the method does not include adjustment of the length of the sample arm optical path. For example, in many embodiments, the viewer assembly includes an objective lens assembly, and the method does not include adjusting a distance between the user's retina and the objective lens assembly.

The lack of adjusting a distance between the user's retina and the objective lens assembly results in a reduced field of view on some user's retinas. To account for such a reduced field of view, in some embodiments, the imaging of the user's retina is limited to a field of view on the user's retina equal to or less than 15 degrees for the reference arm length equal to each of all lengths within the reference arm length adjustment range. In some embodiments, the imaging of the user's retina is limited to a field of view on the user's retina equal to or less than 10 degrees for the reference arm length equal to each of all lengths within the reference arm length adjustment range.

In some embodiments of the method, the OCT imaging device has a relatively small image depth. For example, the OCT imaging device can have an image depth of no more than 3 mm.

In some embodiments of the method, the OCT imaging device has a relatively large sensitivity roll-off. For example, the OCT imaging device can have a sensitivity roll off of not better than −3 db at 2 mm.

In many embodiments of the method, the user specific range of reference arm lengths is substantially smaller than the reference arm length adjustment range. For example, the user specific range of reference arm lengths can be less than half of the reference arm length adjustment range. In some embodiments of the method, the user specific range of reference arm lengths is less than one-quarter of the reference arm length adjustment range.

The method can be practiced using any suitable control unit. For example, in many embodiments, the method includes (a) receiving, by the control unit, input of the user specific range of reference arm lengths, and (b) storing, by the control unit, the user specific range of reference arm lengths in a tangible memory device. In many embodiments, the method includes (a) controlling, by the control unit, the reference arm length adjustment module during an imaging of the user's retina to vary the reference arm length to search within the reference arm length adjustment range to identify a user specific imaging reference arm length for which the OCT image detector produces an OCT signal corresponding to the user's retina, (b) determining, by the control unit, the user specific range of reference arm lengths based on the user specific imaging reference arm length, (c) storing, by the control unit, the user specific range of reference arm lengths in a tangible memory device.

The reference arm length adjustment range can encompass a relatively large range of reference arm lengths. For example, in many embodiments of the method, the reference arm length adjustment range encompasses at least a 20 mm range of reference arm lengths. The reference arm length adjustment range can encompass at least a 30 mm range of reference arm lengths. In some embodiments of the method, the reference arm length adjustment range encompasses at least a 40 mm range of reference arm lengths.

The user specific range of reference arm lengths can encompass a relatively small range of reference arm lengths. For example, in many embodiments of the method, the user specific range of reference arm lengths encompasses less than a 10 mm range of reference arm lengths. The user specific range of reference arm lengths can encompass less than a 6 mm range of reference arm lengths. In some embodiments of the method, the user specific range of reference arm lengths encompasses less than a 4 mm range of reference arm lengths.

The user specific range of reference arm lengths can be determined using any suitable approach. For example, in some embodiments, the method includes (a) receiving, by the control unit, input of the user specific range of reference arm lengths, and (b) storing, by the control unit, the user specific range of reference arm lengths in a tangible memory device. In some embodiments, the method includes (a) controlling, by the control unit, the reference arm length adjustment module during an imaging of the user's retina to vary the reference arm length to search within the reference arm length adjustment range to identify a user specific imaging reference arm length for which the OCT image detector produces an OCT signal corresponding to the user's retina, (b) determining, by the control unit, the user specific range of reference arm lengths based on the user specific imaging reference arm length, and (c) storing, by the control unit, the user specific range of reference arm lengths in a tangible memory device.

In some embodiments of the method, a sensor is used to measure a position of the user relative to the housing. For example, in some embodiments, the method includes (a) generating, by a sensor, a signal indicative of a position of a feature of the user's head relative to the housing, and (b) determining, by the control unit, the user specific range of reference arm lengths based on the signal indicative of a position of a feature of the user's head relative to the housing. In some embodiments, the method includes (a) generating, by a sensor, a signal indicative of a position of a feature of the user's forehead relative to the housing, and (b) determining, by the control unit, the user specific range of reference arm lengths based on the signal indicative of the position of the feature of the user's forehead relative to the housing. In some embodiments, the method includes (a) generating, by a sensor, a signal indicative of a position of a feature an eye of the user relative to the housing, the eye including the user's retina, and (b) determining, by the control unit, the user specific range of reference arm lengths based on the signal indicative of the position of the feature of the eye of the user relative to the housing.

In many embodiments of the method, the viewer assembly includes a compliant member that accommodates an amount of relative movement between the user and the OCT device. For example, in many embodiments of the method, the viewer assembly includes a compliant member having a thickness that can change up to 10 mm in response to change in pressure applied to the viewer assembly by the user's head. In some embodiments of the method, the viewer assembly includes a compliant member having a thickness that can change up to 20 mm in response to change in pressure applied to the viewer assembly by the user's head.

In many embodiments of the method, the ophthalmic imaging system includes a focusing module that is controllable to focus sample light transmitted over the sample arm optical path onto the retina. The method can include: (a) storing, by the control unit, a focus setting of a focusing module of the OCT imaging device corresponding to the user specific range of reference arm lengths, and (b) employing the focus setting during imaging of the user's retina.

In another aspect, an ophthalmic imaging system for imaging a user's retina includes an optical coherence tomography (OCT) imaging device, a housing to which the OCT imaging device is attached, a viewer assembly coupled with the housing, an objective lens assembly, and a control unit. The OCT imaging device includes a sample arm optical path, an OCT image detector, a reference arm optical path having a reference arm length, and a reference arm length adjustment module controllable to vary the reference arm length over a reference arm length adjustment range. The viewer assembly is configured to engage a user's head to restrain the user's head relative to the housing so that the sample arm optical path extends to the user's retina. The ophthalmic imaging system does not include an adjustment mechanism configured to adjust a distance between the user's retina and the objective lens assembly. The control unit is operatively connected to the OCT image detector and the reference arm length adjustment module. The control unit is configured to control the reference arm length adjustment module to vary the reference arm length to identify a reference arm length for which the OCT image detector produces an OCT signal corresponding to the user's retina.

In many embodiments, the ophthalmic imaging system images a reduced field of view on the user's retina. For example, in many embodiments, the ophthalmic imaging system is configured to image a field of view on the user's retina equal to or less than 15 degrees for the reference arm length equal to each of all lengths within the reference arm length adjustment range. In some embodiments, the ophthalmic imaging system is configured to image a field of view on the user's retina equal to or less than 10 degrees for the reference arm length equal to each of all lengths within the reference arm length adjustment range.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
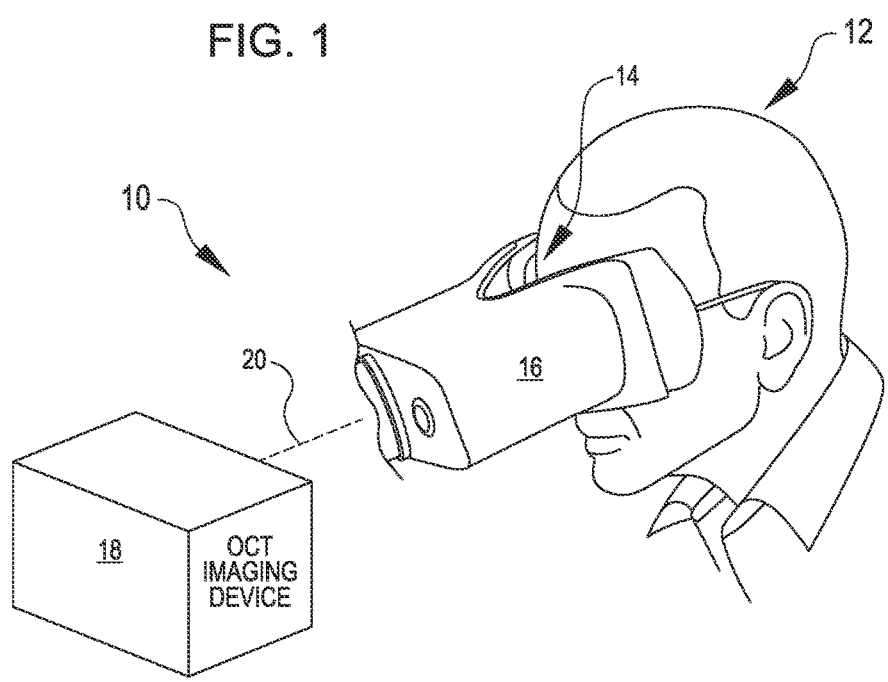
FIG. 1 shows a user engaged with a viewer assembly of an ophthalmic imaging system that includes an OCT imaging device, in accordance with embodiments.

Referring now to the drawings, in which like reference numerals represent like parts throughout the several views, FIG. 1 shows a user 12 looking into a view port 14 of a viewer assembly 16 of an ophthalmic imaging system 10, in accordance with many embodiments. The ophthalmic imaging system 10 includes an optical coherence tomography (OCT) imaging device 18 to which the viewer assembly 16 is coupled. The viewer assembly 16 is configured to be engaged by the user's head to restrain the user's head relative to the OCT imaging device 18 to approximately position one eye of the user 12 on an optical axis of the OCT imaging device 18. For example, in the configuration shown in FIG. 1, the viewer assembly 16 is configured to approximately position the right eye of the user 12 on the optical axis of the OCT imaging device 18. In the illustrated embodiment, the viewer assembly 16 can be rotated, relative to the OCT imaging device 18, 180 degrees around a pivot axis 20 so as to reconfigure the viewer assembly 16 to approximately position the left eye of the user 12 on the optical axis of the OCT imaging device 18. Accordingly, each of the right and the left eye of the user 12 can be selectively approximately positioned on the optical axis of the OCT imaging device 18 for imaging of the respective eye by the OCT imaging device 18. In many embodiments, final positioning and alignment of the optical axis of the respective eye of the user 12 with the optical axis of the OCT imaging device 18 is accomplished by the user 12 adjusting the position of the user's head relative to the view port 14 in response to feedback provided to the user 12 by the ophthalmic imaging device 18.

Figure 2:
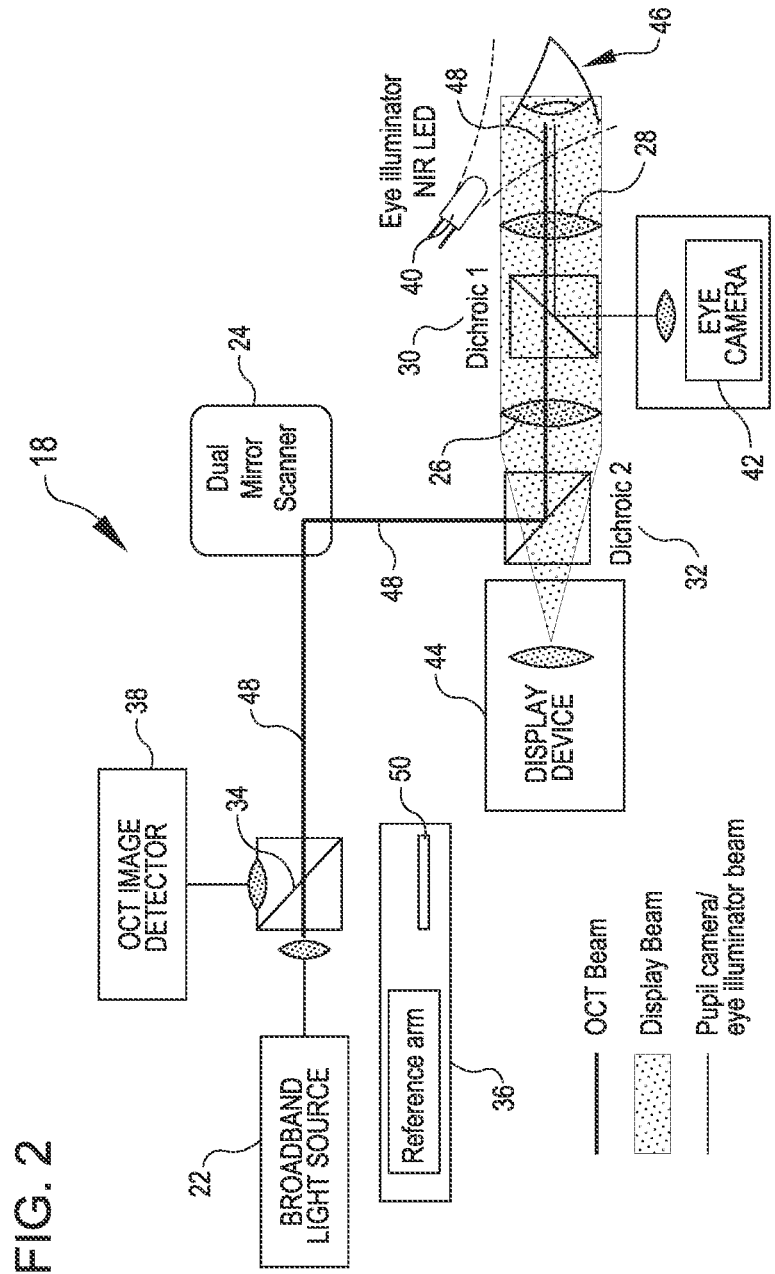
FIG. 2 is a simplified schematic illustration of components and associated optical paths of the OCT imaging device of the ophthalmic imaging system of FIG. 1.

In many embodiments, the OCT imaging device 18 automatically adjusts the reference arm path length as described herein during imaging session in which an OCT image is generated for a user's retina. The OCT imaging device 18 can have any suitable configuration that accommodates automatic adjustment of reference arm path length. For example, FIG. 2 shows a simplified schematic illustration of components and associated optical paths of an embodiment of the OCT imaging device 18. The components of the OCT imaging device 18 illustrated in FIG. 2 include a broadband light source 22, a dual mirror scanner 24, focusing lenses 26, 28, dichroic mirrors 30, 32, 34, an adjustable reference arm module 36, an OCT image detector 38, an eye illuminator 40, an eye camera 42, and a display device 44. In the illustrated embodiment, the OCT imaging device 18 is a spectral domain OCT imaging device that operates in a wavelength range of 800 nm to 900 nm. The eye illuminator 40 illuminates an eye 46 of the user 12 using a suitable wavelength of light (e.g., a wavelength of light above 920 nm). The display device 44 can project light between any suitable wavelength (e.g., from 400 nm to 700 nm). The dichroic mirror 30 transmits the OCT wavelength and the display wavelength range (400 nm to 900 nm) and reflects the illumination wavelength (e.g., greater than 920 nm) to the eye camera 40. The dichroic mirror 32 transmits the display wavelength range and reflects the OCT wavelength.

In operation, the broadband light source 22 generates the OCT wavelength light. The OCT wavelength light propagates from the light source 22 to the dichroic mirror 34. A sample arm portion of the OCT wavelength light passes through the dichroic mirror 34 and proceeds to propagate along a sample arm optical path 48 to the eye 46. A reference arm portion of the OCT wavelength light is reflected by the dichroic mirror 34 so as to propagate along a reference arm optical path that extends into the adjustable reference arm module 36. The sample arm portion of the OCT wavelength light is focused on the retina of the eye 46. The OCT wavelength light focused on the retina is scattered by the retina so that a backscattered portion of the OCT wavelength light propagates back along the sample arm optical path 48. The backscattered portion of the OCT wavelength light passes through the dichroic mirror 30, is reflected by the dichroic mirror 32 and the dual scanning mirror 24 back to the dichroic mirror 34, which reflects the backscattered portion of the OCT wavelength light to the OCT image detector 38. The adjustable reference arm module 36 includes a reference arm mirror 50 that reflects the reference arm portion of the OCT wavelength light back to the dichroic mirror 34. The returning portion of the reference arm portion of the OCT wavelength light passes through the dichroic mirror 34 to the OCT image detector 38. In response to the combined incidence of the returning sample arm OCT light and the returning reference arm OCT light onto the OCT image detector 38, the OCT image detector 38 generates and outputs an OCT image signal that is processed using known techniques to build up a three-dimensional OCT image of layers of the retina. In many embodiments, the OCT image detector 38 detects interference between the returning sample arm light and the reference arm light only if the time travelled by light in the reference and sample arms is nearly equal. In many embodiments, the reference arm mirror 50 is mounted to a motorized mechanism that is controllable to vary the position of the reference arm mirror 50, thereby controllably varying the reference arm optical path length. The ability to vary the reference arm path length enables the OCT imaging device 18 to be used to generate OCT images of any user's retina of a desired population of users even though each user's retina can be at a different distance from the OCT imaging device 18 when the user's head is engaged with the viewer assembly 16 due to corresponding anatomical variations between user's heads, as well as variation in the relative position between the user's head and the viewer assembly 16.

In many embodiments, the eye illuminator 40, the eye camera 42, and the display device 44 are used to provide feedback to the user 12 by which the user 12 self-aligns the eye 46 with the optical axis of the OCT imaging device 18. The display device 44 displays a fixation target that is viewed by the user so as to align the eye 46. The eye camera 42 measures the current position of the eye relative to the optical axis of the OCT imaging device 18 via illumination of the eye 46 by the eye illuminator 40. Based on the measured position of the eye relative to the optical axis of the OCT imaging device 18, the display device 44 further displays feedback to the user 12 by which the user adjusts the position of the user's head relative to the viewer assembly 16 to position the user's eye 46 within an acceptable distance of the optical axis of the OCT imaging device 18 for the generation of an OCT image of the user's retina.

Figure 3:
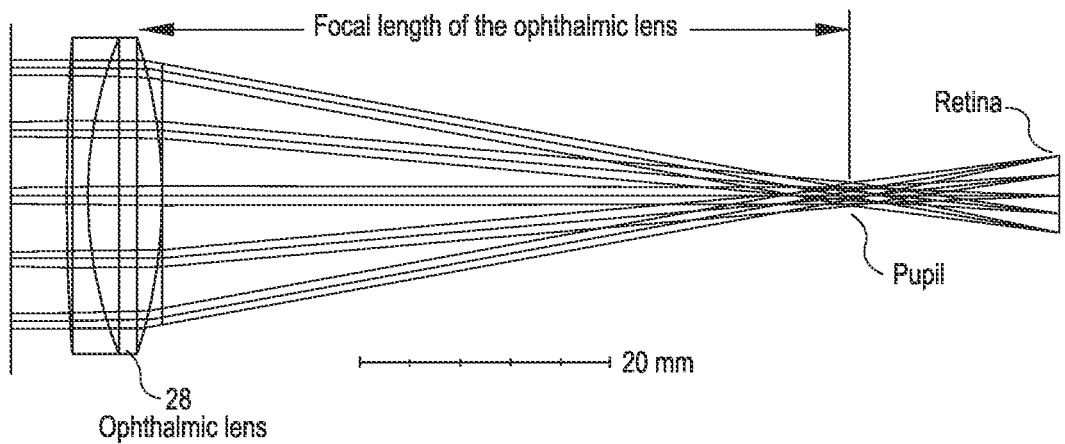
FIG. 3 illustrates field of view on the retina when the pupil is positioned at the focal length of an ophthalmic lens of an ophthalmic OCT imaging system.
Figure 4:
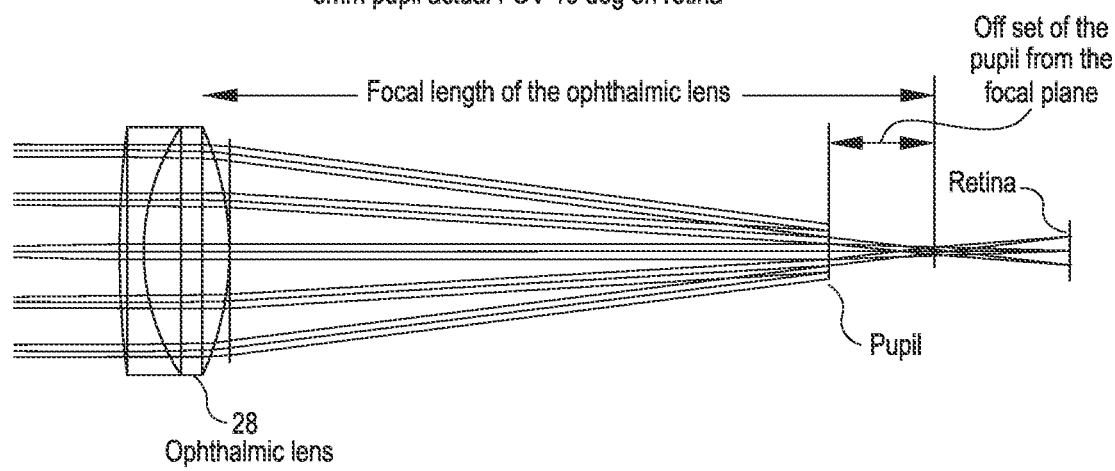
FIG. 4 illustrates a reduced field of view on the retina when the pupil is positioned away from the focal length of an ophthalmic lens of an ophthalmic OCT imaging system.

As illustrated in FIG. 3, positioning the pupil at the focal length of the ophthalmic lens 28 maximizes the area on the retina that can be imaged by minimizing the amount of sample arm portion of the OCT wavelength light that is obscured by the iris. In contrast, as illustrated in FIG. 4, positioning the pupil away from the focal length of the ophthalmic lens 28 reduces the area on the retina that can be imaged. Accordingly, in order to image a visual field of the entire macula (about 20 degrees), existing ophthalmic OCT systems include a means to adjust the distance between the pupil and the ophthalmic lens of the OCT system. In some existing ophthalmic OCT systems, the distance between the entire ophthalmic OCT system and the user's pupil is adjustable. In some other existing ophthalmic OCT systems, the position of the ophthalmic lens relative to the rest of the ophthalmic OCT system is adjustable so as to adjust the distance between the ophthalmic lens and the user's pupil. In some other existing ophthalmic OCT systems, the position of the user's head is moved relative to the ophthalmic OCT system to adjust the distance between the ophthalmic lens and the user's pupil.

In existing ophthalmic OCT systems, elimination of the ability to reposition the pupil relative to the ophthalmic lens would seriously degrade performance. For example, in existing ophthalmic OCT systems, elimination of the ability to reposition the pupil relative to the ophthalmic lens can result in: (a) a large reduction in the field of view on the retina due to obstruction by the iris, and/or (b) inability to adjust the reference arm path length to a length required for imaging the retina where the existing ophthalmic OCT system lacks sufficient adjustment range for the reference arm path length.

In contrast to existing ophthalmic OCT systems, in many embodiments of the ophthalmic OCT systems described herein, the distance between the user's pupil and the ophthalmic lens is substantially fixed and the ophthalmic OCT system does not include an adjustment mechanism configured to adjust the distance between the user's pupil and the objective lens assembly. To accommodate the lack of an adjustment mechanism configured to adjust the distance between the user's pupil and the objective lens assembly, the adjustable reference arm module 36 is configured to be controllable to vary the reference arm path length over a reference arm path length adjustment range that is significantly larger than in current ophthalmic OCT systems. For existing ophthalmic OCT imaging systems, adjustment of the reference arm path length only needs to accommodate variation in the axial length of the eye for different users. Typical axial length of the eye can vary by +/−3 mm for (+/−6 Diopter). As a result, adjustment to the reference arm path length in existing OCT imaging systems does not need to exceed about 6 mm. In contrast, variation in the location of facial landmarks relative to the eye are much greater. Facial land marks can vary in a range of +/−30 mm. Accordingly, in many embodiments, the reference arm length adjustment range encompasses a relatively large range of reference arm lengths. For example, in many embodiments of the method, the reference arm length adjustment range encompasses at least a 20 mm range of reference arm lengths. The reference arm length adjustment range can encompass at least a 40 mm range of reference arm lengths. In some embodiments of the method, the reference arm length adjustment range encompasses at least a 60 mm range of reference arm lengths.

The larger reference arm path length adjustment range, however, by itself, would increases the time it takes to search within the larger reference arm path length adjustment range to identify a reference arm length for which the OCT image detector 38 produces an OCT signal corresponding to the user's retina. Increased search time significantly increases chair time resulting in fixation losses and increased technician cost. To limit the search time, in many embodiments described herein, a user specific range of reference path arm lengths is employed to limit the search to identify the reference arm length for which the OCT image detector produces an OCT signal corresponding to the user's retina to a suitably small range of reference arm lengths for the specific user.

Any suitable approach, such as those described herein, can be used to determine a suitable user specific range of reference path arm lengths for a particular user. For example, as described herein, the larger reference arm path length adjustment range of the adjustable reference arm module 36 can be searched during an initial imaging of the user's retina to identify a reference path length for which the OCT image detector 38 produces an OCT signal corresponding to the user's retina. The identified reference path length for the initial imaging of the user's retina can then be used to formulate a suitable user specific range of reference path arm lengths for use in subsequent imaging sessions of the specific user's retina. Alternatively, a suitable user specific range of reference path arm lengths for any particular user can be predetermined based on spatial information about a user's facial features (e.g., forehead, cheeks, cornea, lateral orbital rim, and/or any other suitable facial feature) and their relations to each other. The spatial information about the user's facial features can be captured/measured in any suitable manner including, but not limited to, any suitable virtual approach, any suitable physical approach, and any suitable combination of virtual and physical approaches. For example, the spatial information about the user's facial features and/or the suitable user specific range of reference path arm lengths can be determined based on: (a) three-dimensional scanning of the user's face, (b) caliper measurement of the specific land mark on the user's face relative to the user's eye ball, (c) a cast mask of the user's face, (d) combinations of (a) through (c) with axial length of the eye (e.g., measured via ultrasound, OCT, etc.) combined with measurement of the distance to the facial land mark to determine the distance of the facial land mark to the retina, and/or (e) OCT measurement via the OCT image detector 38.

Moreover, without an adjustment mechanism to adjust the distance between the user's pupil and the objective lens assembly, a reduced field of view of the user's retina can result for some users, such as users with small pupils that are positioned away from the focal length of the ophthalmic lens 28. To accommodate variability in the resulting field of view for different users, in some embodiments, the ophthalmic imaging system 10 images a fixed reduced field of view for all users. For example, in some embodiments, the ophthalmic imaging system 10 is configured to image a field of view on the user's retina equal to or less than 15 degrees for the reference arm length equal to any length within the reference arm length adjustment range. In some embodiments, the ophthalmic imaging system 10 is configured to image a field of view on the user's retina equal to or less than 10 degrees for the reference arm length equal to any length within the reference arm length adjustment range.

Figure 5:
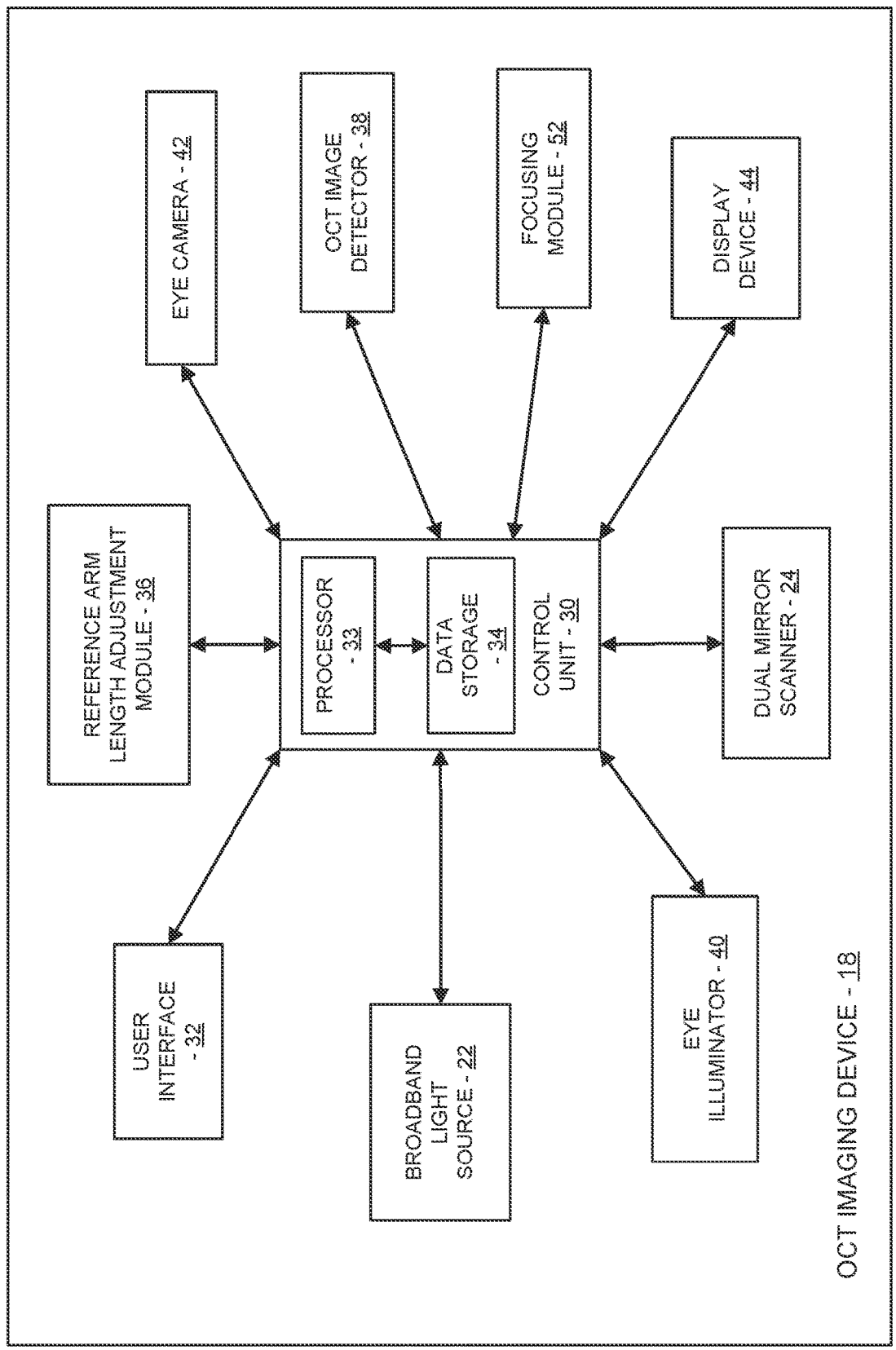
FIG. 5 is a simplified schematic diagram of components of the OCT imaging device of the ophthalmic imaging system of FIG. 1.

In many embodiments, the OCT imaging device 18 is configured to automatically control components/modules of the OCT imaging device 18 during a imaging session during which an OCT image of a user's retina is generated. In many embodiments, the OCT imaging device 18 includes a suitable control unit that is operatively connected to components/modules of the OCT imaging device 18 and configured to communicate and/or control the components/modules. For example, FIG. 5 is a simplified schematic diagram illustrating components/modules of an embodiment of the OCT imaging device 18 that includes a control unit 30 operatively coupled with the components/modules. The control unit 30 includes a processor 33 and a data storage device 34. The data storage device 34 stores program instructions executable by the processor 33 to accomplish the acts described herein. The data storage device 34 also stores user specific data as described herein that is used by the processor 33 to customize its control of the operation of the OCT imaging device 18 to the specific user as described herein.

The control unit 30 is operatively connected to the a user interface 32 to receive input from the user via the user interface 32 and/or to display output to the user via the user interface 32. Any suitable user interface 32 can be employed including, but not limited to, one or more push buttons, a display, a touch display, one or more indicator lights, and/or a speaker. The user interface 32 can be configured to enable a user to input an identification of the user for a imaging session so that the control unit 30 can employ scanning parameters stored in the data storage device 34 when controlling the components/modules of the OCT imaging device 18 during a imaging session for the user.

The control unit 30 is operatively connected to the eye illuminator 40, the eye camera 42, and the display device 44. The control unit 30 can turn the eye illuminator 40 on at the start of a imaging session and off at the end of a imaging session. In many embodiments, the control unit 30 turns the eye camera 42 on at the start of the imaging session, receives image data from the eye camera 42, processes the image data to track the position of the optical axis of the eye 46 relative to the optical axis of the OCT imaging device 18, and turns the eye camera 42 off at the end of the imaging session. In many embodiments, the control unit 30 turns the display device 44 on at the start of the imaging session, generates and displays feedback to the user on the display device 44 to enable the user to reposition the user's head relative to the viewer assembly 16 to sufficiently align the user's eye 46 with the optical axis of the OCT imaging device 18 for the generation of an OCT image of the user's retina, and turns the display device 44 of that the end of the imaging session.

The control unit 30 is operatively connected to the broadband light source 22, the dual mirror scanner 24, the reference arm length adjustment module 36, the OCT image detector 38, and a focusing module 52 to control operation of these components/modules during an OCT imaging portion of a imaging session. The control unit 22 can turn the broadband light source 22 on to begin transmission of the OCT wavelength light over the sample and reference arms at the beginning of the OCT scanning portion of the imaging session, and can turn the light source 22 off to at the end of the imaging session. The control unit 30 can control the reference arm length adjustment module 36 to vary the reference arm length to search for a user specific reference arm length(s) as described herein for the respective user for which the OCT image detector 38 generates a suitable OCT signal for use in generating an OCT image of the user's retina. The control unit 30 can control the reference arm length adjustment module 36 to vary the reference arm length to search within a previously determined user specific range of reference arm lengths for the respective user to identify a reference arm length for which the OCT image detector 38 generates a suitable OCT signal for use in generating an OCT image of the user's retina. The control unit 30 can also control the reference arm length adjustment module 36 so as to optimize the OCT signal generated by the OCT image detector 38 and/or to adjust the reference arm length in response to movement of the eye 46 relative to the OCT imaging device 18. In many embodiments, the control unit 30 stores, in the data storage device 34, one or more reference arm lengths and/or one or more settings of the reference arm length adjustment module 36 for which the OCT image detector 38 is found to generate a suitable OCT signal during a imaging session for a user for use in conjunction with control of the reference arm length adjustment module 36 during a subsequent imaging session of the user as described herein. In many embodiments, the control unit 30 stores, in the data storage device 34, a previously determined user specific range of reference arm lengths, for the respective user, that is searched during imaging of the user's retina to identify a reference arm length for which the OCT image detector 38 generates a suitable OCT signal for use in generating an OCT image of the user's retina. The control unit 30 can control the focusing module 52 to vary a setting of the focusing module 52 to focus the sample arm OCT wavelength light onto a target surface of the retina of the eye 46. The control unit 30 can store, in the data storage device 34, a suitable setting of the focusing module 52 used during a imaging session for a user for use as the setting of the focusing module 52 during a subsequent imaging session of the user as described herein. In many embodiments, the control unit 30 turns the OCT image detector 38 on at the start of the OCT scanning portion of the imaging session, receives an OCT detector output signal generated by the OCT image detector 38, processes the OCT detector output signal to generate an OCT image of the retina and to determine how to control the reference arm length adjustment module 36 and the focusing module 52 during a imaging session, and turns the OCT image detector 38 off at the end of the imaging session. In many embodiments, the control unit 30 controls the operation of the dual mirror scanner 24 during a imaging session. During an initial portion of a imaging session, the control unit 30 can control the dual mirror scanner 24 to perform a limited two-dimensional scan of the sample arm OCT wavelength light suitable for searching for suitable settings of the reference arm length adjustment module 36 and/or the focusing module 52 for which the OCT image detector 38 generates a suitable OCT detector output signal for the generation of an OCT image of the retina. Once suitable settings of the reference arm length adjustment module 36 and/or the focusing module 52 are determined by the control unit 30, the control unit 30 can control operation of the dual mirror scanner 24 to perform a two-dimensional scan of the sample arm OCT wavelength light suitable for the generation of an OCT image of the retina.

Figure 6:
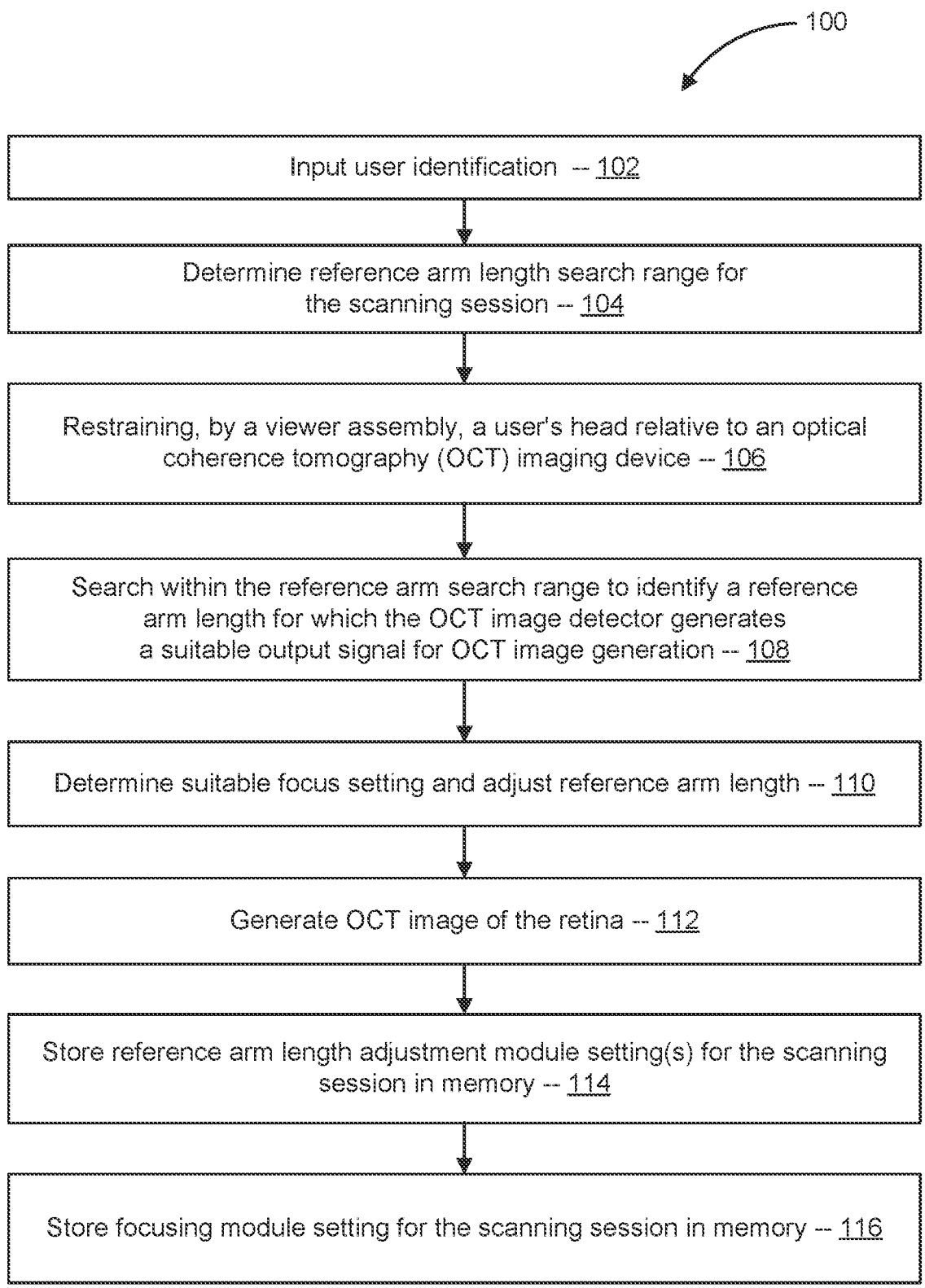
FIG. 6 is a simplified schematic block diagrams of acts of a method of imaging a retina during an imaging session, in accordance with embodiments.

FIG. 6 is a simplified schematic block diagrams of acts of a method 100 of imaging a retina by an ophthalmic imaging system during an imaging session, in accordance with embodiments. Any suitable ophthalmic imaging system, such as the ophthalmic imaging system 10 described herein, can be used to practice the method 100.

In act 102, an identification of a user of the ophthalmic imaging system is input to the ophthalmic imaging system for use in controlling an OCT imaging device of the ophthalmic imaging system during an imaging session. For example, the identification of the user can be used to retrieve user specific reference arm length data and/or user specific focus data for use in controlling the OCT imaging device during the imaging session. The identification of the user can also be used to store user specific reference arm length data and/or user specific focus data determined during the imaging session for use in one or more subsequent imaging sessions for the identified user.

Figure 7:
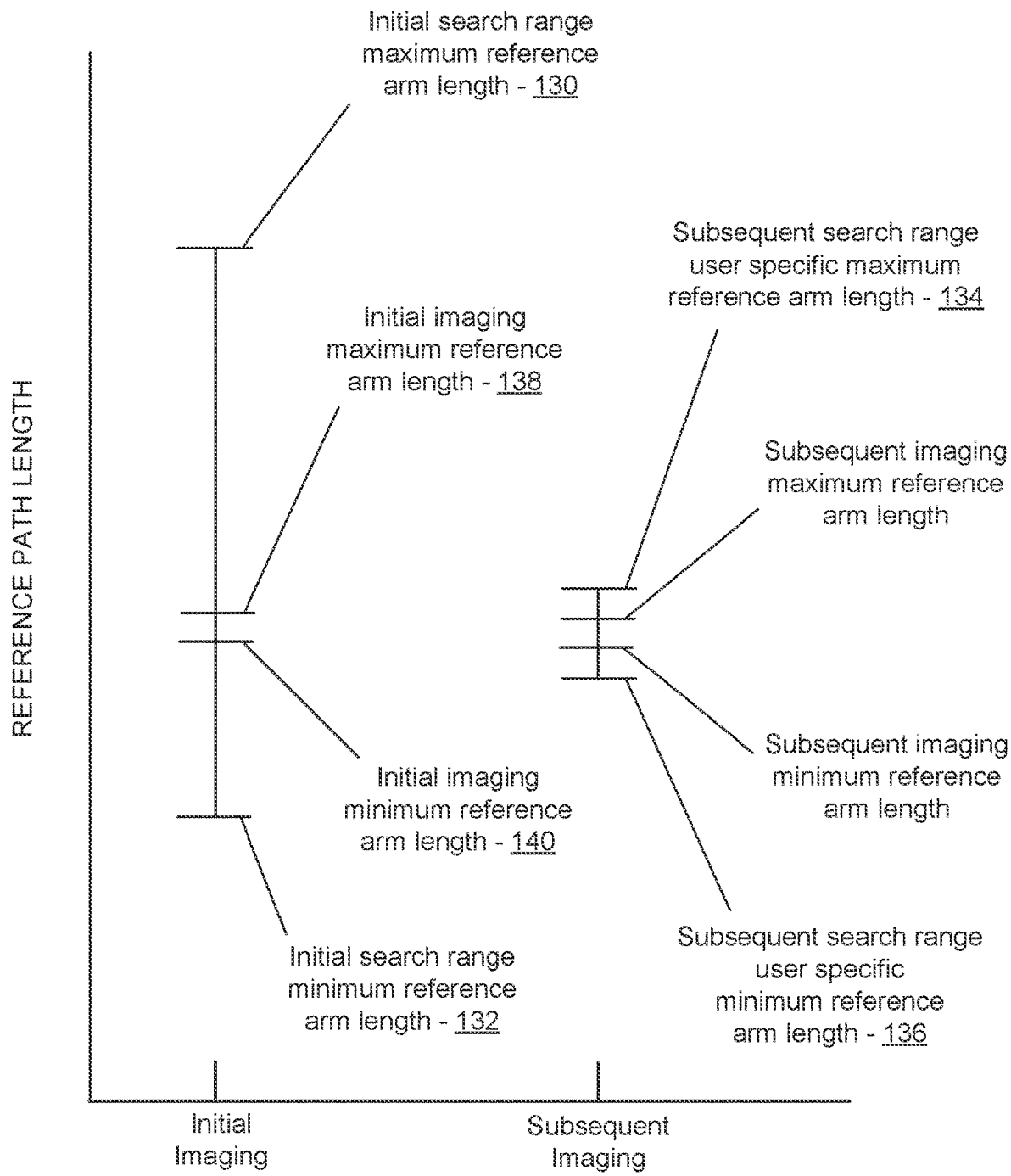
FIG. 7 illustrates example search ranges for reference arm path length for an initial imaging of a particular user's retina and a subsequent imaging of the particular user's retina, in accordance with embodiments.

In act 104, the identification of the user for the imaging session can be used to determine a suitable reference arm search range for the imaging session. If no reference arm length data is stored for the identified user, the reference arm search range for the imaging session can be set to a default initial search range suitable for a target population of users that includes the identified user. For example, FIG. 7 illustrates example search ranges for the reference arm path length of the OCT imaging device for an initial imaging of a user's retina and a subsequent imaging of the user's retina. The search range for the reference arm path length for a subsequent imaging of a user's retina will typically be smaller than the search range for the reference arm path length for the initial imaging of the user's retina because the search range for the subsequent imaging is determined based on the reference arm path lengths used to generate an OCT image of the user's retina during an earlier imaging session(s). During an initial imaging session of the identified user's retina, the reference arm search range for the imaging session can be defined between an initial search range maximum reference arm length 130 and an initial search range minimum reference arm length 132 suitable for the target population of users. During a subsequent imaging session of the identified user's retina, the reference arm search range for the imaging session can be defined between a user specific maximum reference arm length 134 and a user specific minimum reference arm length 136 based on reference arm lengths used to image the user's retina during one or more previous imaging sessions. For example, the user specific maximum reference arm length 134 can be set by adding a suitable path length increment to an initial imaging maximum reference arm length 138 employed to generate an OCT image of the user's retina during an initial imaging session for the identified user. Likewise, the user specific minimum reference arm length 136 can be set by subtracting a suitable path length increment to an initial imaging minimum reference arm length 140 employed to generate an OCT image of the user's retina during an initial imaging session for the identified user.

In act 106, the user's head is engaged with a viewer assembly so as to restrain the position of the user's head relative to the OCT imaging device during the imaging session. In many embodiments, the OCT imaging device provides feedback to the user to enable the user to reposition the user's head to position the user's eye to be imaged within a suitable distance from the optical axis of the OCT imaging device and in suitable alignment with the optical axis of the OCT imaging device for the generation of an OCT image of the user's retina.

In act 108, with the user's eye suitably restrained relative to the optical axis of the OCT imaging device, the reference arm length of the OCT imaging device is varied to search within the reference arm search range for the imaging session to identify a suitable reference arm length for use in generating an OCT image of the user's retina. For example, in the OCT imaging device 18, the position of the reference arm mirror 50 is controlled by the control unit 30 to vary the reference arm length within the reference arm search range for the imaging session. The OCT image detector output signal is monitored by the control unit 30 to identify a reference arm length for which the OCT image detector output signal indicates that the reference arm length matches the sample arm length close enough for the generation of an OCT image for the user's retina. To speed the search for a suitable reference arm length for the imaging session, the extent to which the sample arm OCT light is scanned in two dimensions during the search for the suitable reference arm length can be limited as compared to the two-dimensional scanning used to generate the OCT image of the retina. When the reference arm search range for the imaging session is based on the reference arm length(s) used to generate an OCT image for the user during one or more previous imaging sessions, the time required to search the resulting user specific reference arm search range may be substantially reduced relative to the time required to search the larger reference arm search range for an initial imaging session for the user.

In act 110, the sample arm OCT wavelength light is focused on the retina and the reference arm length is adjusted, if necessary, to optimize the OCT image detector output signal. For example, in the OCT imaging device 18, the control unit 30 can control the focusing module 52 to vary the optical power of the focusing module 52 to vary the focus of the sample arm OCT wavelength light over a target surface of the retina while monitoring the OCT image detector output signal to identify a setting for the focusing module 52 that optimizes the OCT image detector output signal for suitable locations on the target surface of the retina. Once an optimum setting for the focusing module 52 is identified, the control unit 30 can control the reference arm length adjustment module 36 to finely vary the reference arm length while monitoring the OCT image detector output signal to identify a setting for the reference arm length adjustment module 36 that optimizes the OCT image detector output signal for the optimal setting of the focusing module 52.

In act 112, the identified reference path length and the identified focus setting are used during generation of an OCT image for the user's retina. In some embodiments, the reference path length is controlled during the generation of the OCT image to optimize the OCT image detector output signal throughout the generation of the OCT image.

In act 114, the reference arm length(s) used to generate the OCT image during the imaging session is stored in a memory device (e.g., the data storage device 34 of the control unit 30) so as to be associated with the identified user for use in determining the reference arm search range for a subsequent imaging session for the identified user. If the reference arm path length was varied during the generation of the OCT image to optimize the OCT image detector output signal throughout the generation of the OCT image and/or in response to movement of the eye relative to the OCT imaging device, a maximum reference arm length and a minimum reference arm length used during the generation of the OCT image can be stored in memory device so as to be associated with the identified user for use in determining the reference arm search range for a subsequent imaging session for the identified user.

In act 116, a focus setting used during the generation of the OCT image can be stored in a memory device so as to be associated with the identified user for use in a subsequent imaging session for the identified user. For example, in the OCT imaging device 18, the control unit 30 can store a setting of the focusing module 52 in the data storage device 34 so as to be associated with the identified user for use as the setting of the focusing module 52 in a subsequent imaging session for the identified user.

Figure 8:
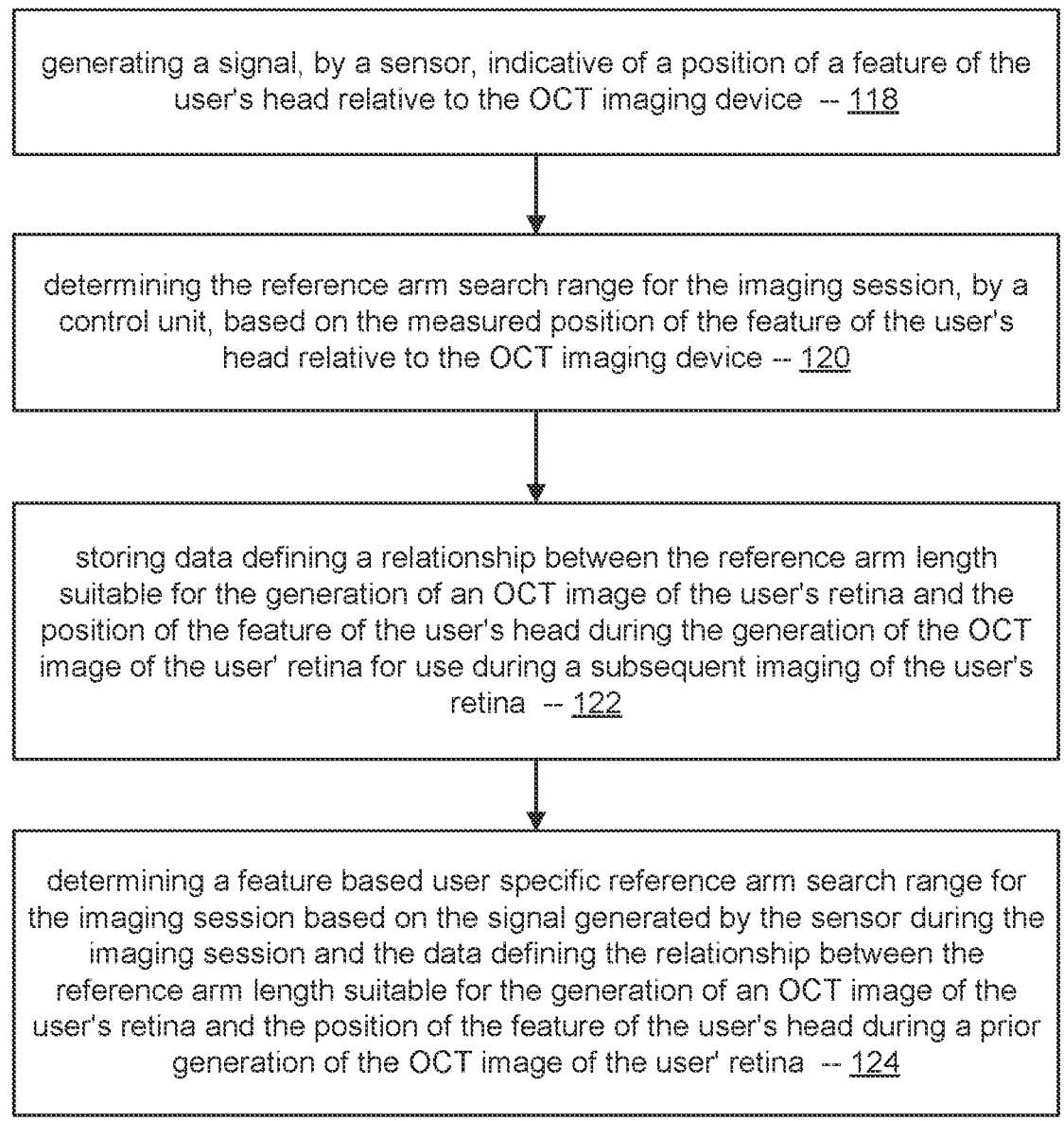
FIG. 8 is a simplified schematic block diagrams of acts for determining a user specific range of reference arm lengths to search during a subsequent imaging session for imaging a user's retina based in part on a sensor measured position of the user, in accordance with embodiments.
Figure 9:
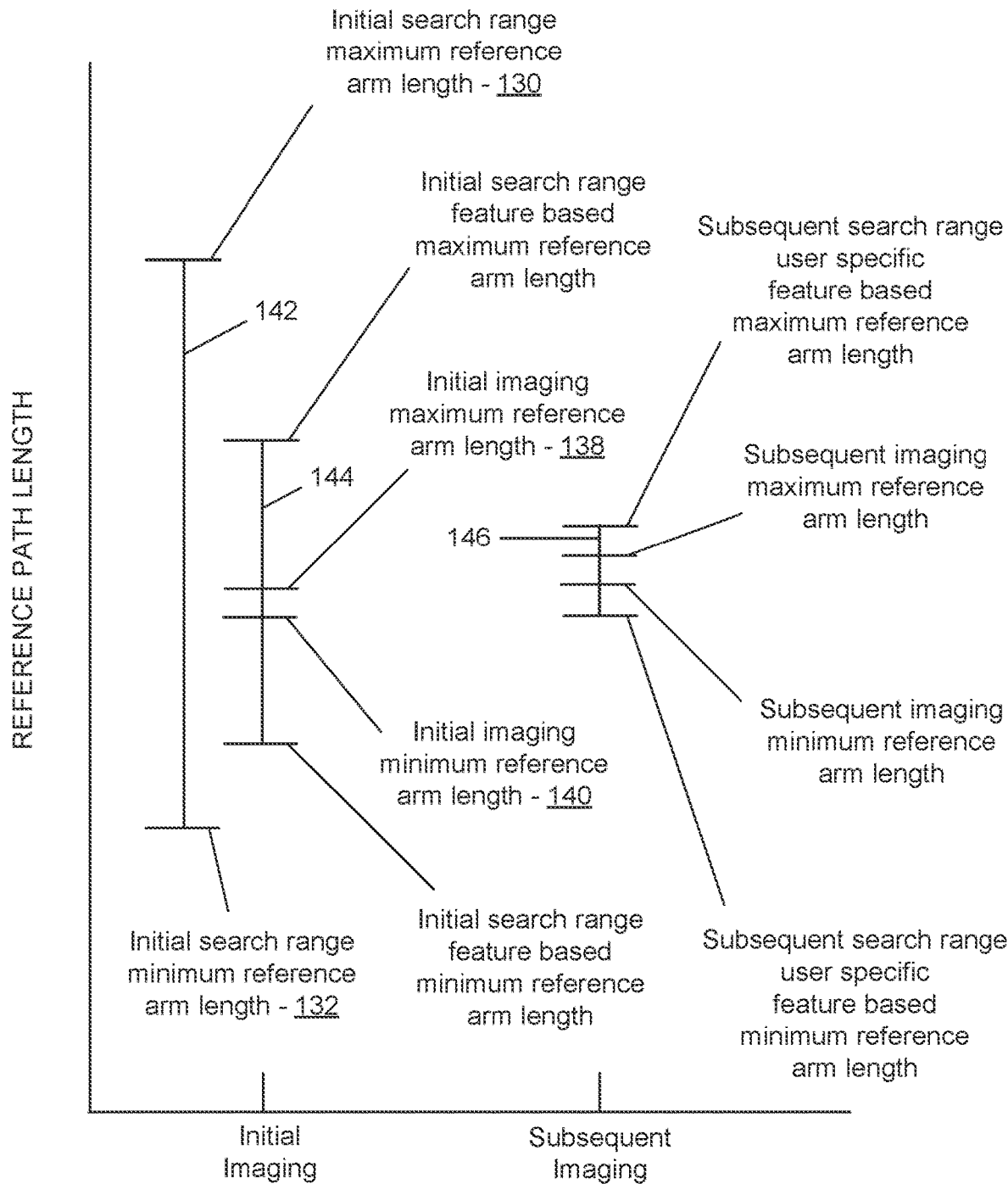
FIG. 9 illustrates example feature based search ranges for reference arm path length for an initial imaging of a particular user's retina and a subsequent imaging of the particular user's retina, in accordance with embodiments.

FIG. 8 is a simplified schematic block diagrams of additional acts that can be accomplished in the method 100 to determine the reference arm search range for a subsequent imaging session for the identified user. In act 118, a sensor generates a signal indicative of a position of a feature of the user's head relative to the OCT imaging device. For example, in the ophthalmic imaging system 10, the sensor can be mounted to the viewer assembly 16 and generate a signal indicative of a position of a feature of the user's head relative to the OCT imaging device 18. In act 120, the measured position of the feature of the user's head relative to the OCT imaging device is used by a control unit to determine the reference arm search range for the imaging session. For example, in embodiments in which the viewer assembly 16 includes a compliant member that deforms by different amounts in response to different interface force magnitudes applied to the viewer assembly 16 by the user's head, the measured position of the feature of the user's head relative to the OCT imaging device can be used to determine the reference arm search range for the imaging session so as to account for the actual gross position of the user's head relative to the OCT imaging device. By accounting for the actual gross position of the user's head relative to the OCT imaging device, the reference arm search range for the imaging session can cover a smaller range of reference arm lengths as compared to when the actual gross position of the user's head relative to the OCT imaging device is unknown. For example, FIG. 9 illustrates an example non-feature based initial reference arm search range 142 suitable for an initial imaging session for a user for which the gross position of the user's head relative to the OCT imaging device is unknown, an example feature based initial reference arm search range 144 suitable for an initial imaging session for a user for which the gross position of the user's head has been measured via a sensor that generates a signal indicative of the position of a feature of the user's head relative to the OCT imaging device, and an example feature based user specific reference arm search range 146 suitable for a subsequent imaging session for a user for which the gross position of the user's head has been measured via a sensor that generates a signal indicative of the position of a feature of the user's head relative to the OCT imaging device. The non-feature based initial reference arm search range 142 can be selected suitable for a target population of users and for a suitable range of expected gross positions between the head of each of the target population of users and the OCT imaging device. The feature based initial reference arm search range 144 can be selected based on a measured gross position of a user's head and the target population of users. By measuring the actual gross position of a user's head relative to the OCT imaging device, the feature based initial reference arm search range 144 covers a smaller range of reference arm lengths that the non-feature based initial reference arm search range 142, which accommodates variation in the possible gross position between the user's head and the OCT imaging device. The feature based user specific reference arm search range 146 covers a smaller range of reference arm lengths that the feature base initial reference arm search range 144 because the feature based user specific reference arm search range 146 is based on both the measured gross position of a specific user's head relative to the OCT imaging device and the reference arm lengths used during the generation of an OCT image of the specific user's retina during one or more previous imaging sessions. In act 122, data defining a relationship between the reference arm length suitable for the generation of an OCT image of the user's retina and the position of the feature of the user's head during the generation of the OCT image of the user' retina is stored in memory for use during a subsequent imaging of the user's retina. In act 124, the signal generated by the sensor during a subsequent imaging session for the user and the data defining the relationship between the reference arm length suitable for the generation of an OCT image of the user's retina and the position of the feature of the user's head during the prior generation of the OCT image of the user' retina are used to determine the feature based user specific reference arm search range 146 for the imaging session.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of imaging a retina of a user, the method comprising:
    generating, by a sensor, a signal indicative of a position of a feature of a user's head relative to an OCT imaging device;
    determining, by a control unit, a user specific reference arm adjustment length range for the user within a reference arm adjustment length range of the OCT device based on the signal indicative of the position of the feature of the user's head relative to the OCT imaging device, wherein the user specific reference arm adjustment length range is smaller than the reference arm adjustment length range; and
    controlling, by the control unit, a reference arm length adjustment module of the OCT imaging device during an imaging of the retina of the user to vary a reference arm length of the OCT imaging device within the user specific reference arm adjustment length range to identify an imaging reference arm length for which an OCT image detector of the OCT imaging device produces an OCT signal corresponding to the retina of the user.

2. The method of claim 1, wherein the position of the feature of the user's head relative to the OCT imaging device is indicative of an overall position of the user's head relative to the OCT imaging device.

3. The method of claim 1, further comprising:
    storing, by the control unit, data defining a relationship between the position of the feature of the user's head relative to the OCT imaging device and the imaging reference arm length for which the OCT image detector produced the OCT signal corresponding to the retina of the user;

generating, by the sensor, a second signal indicative of a second position of the feature of the user's head relative to an OCT imaging device;

determining, by the control unit, a user specific second reference arm adjustment length range for the user within the reference arm adjustment length range of the OCT device based on the second signal indicative of the second position of the feature of the user's head relative to the OCT imaging device, wherein the user specific second reference arm adjustment length range is smaller than the reference arm adjustment length range and different from the user specific reference arm adjustment length range; and controlling, by the control unit, the reference arm length adjustment module during a second imaging of the retina of the user to vary the reference arm length of the OCT imaging device within the user specific second reference arm adjustment length range to identify a second imaging session reference arm length for which the OCT image detector produces an OCT signal corresponding to the retina of the user.

4. The method of claim 1, further comprising restraining, by a viewer assembly engaged with the user's head so that a sample arm optical path of an optical coherence tomography (OCT) imaging device extends to the retina of the user.

5. The method of claim 4, wherein the user specific reference arm adjustment length range is based on spatial information about one or more facial features of the user.

6. The method of claim 5, wherein the one or more facial features of the user comprise one or more of a forehead of the user, one or more cheeks of the user, a cornea of an eye of the user including the retina of the user, and a lateral orbital rim of the user.

7. The method of claim 5, wherein the spatial information about one or more facial features of the user is generated via one or more of:
three-dimensional scanning of the one or more facial features of the user;
caliper measurement of the one or more facial features of the user relative to an eye of the user that includes the retina of the user;
a cast mask of the one or more facial features of the user;
an axial length of the eye of the user that includes the retina of the user;
ultrasound measurement of the axial length of the eye of the user that includes the retina of the user; and
OCT measurement of the axial length of the eye of the user that includes the retina of the user.

8. The method of claim 6, wherein:
the OCT imaging device comprises an objective lens assembly; and
a distance between the retina of the user and the objective lens assembly is not adjusted.

9. The method of claim 8, wherein the imaging of the retina of the user is limited to a field of view on the retina of the user equal to or less than 15 degrees for the reference arm length equal to each of all lengths within the reference arm length adjustment range.

10. The method of claim 9, wherein the imaging of the retina of the user is limited to a field of view on the retina of the user equal to or less than 10 degrees for the reference arm length equal to each of all lengths within the reference arm length adjustment range.

11. The method of claim 1, wherein the OCT imaging device has an image depth of no more than 3 mm.

12. The method of claim 11, wherein the OCT imaging device has a sensitivity roll off of not better than −3db at 2 mm.

13. The method of claim 1, wherein the user specific reference arm adjustment length range encompasses less than half of the reference arm length adjustment range.

14. The method of claim 13, wherein the user specific reference arm adjustment length range encompasses less than one-quarter of the reference arm length adjustment range.

15. The method of claim 1, wherein the reference arm length adjustment range encompasses at least a 20 mm range of reference arm lengths.

16. The method of claim 15, wherein the reference arm length adjustment range encompasses at least a 30 mm range of reference arm lengths.

17. The method of claim 16, wherein the reference arm length adjustment range encompasses at least a 40 mm range of reference arm lengths.

18. The method of claim 1, wherein the user specific reference arm adjustment length range encompasses less than a 10 mm range of the reference arm length adjustment range.

19. The method of claim 18, wherein the user specific reference arm adjustment length range encompasses less than a 6 mm range of the reference arm length adjustment range.

20. The method of claim 19, wherein the user specific reference arm adjustment length range encompasses less than a 4 mm range of the reference arm length adjustment range.

* * * * *